United States Patent
Sheldon et al.

(10) Patent No.: US 10,539,808 B2
(45) Date of Patent: Jan. 21, 2020

(54) IMPACT ABSORBING ELEMENTS FOR EYEWEAR, INCLUDING OVERMOLDED EYEWEAR

(71) Applicant: Brent Sheldon, Miami Beach, FL (US)

(72) Inventors: Brent Sheldon, Miami Beach, FL (US); Guy Brousseau, Jr., Marieville (CA)

(73) Assignee: Brent Sheldon, Miami Beach, FL (US)

(*) Notice: Subject to any disclaimer, the term of this patent is extended or adjusted under 35 U.S.C. 154(b) by 0 days.

(21) Appl. No.: 15/629,813

(22) Filed: Jun. 22, 2017

(65) Prior Publication Data

US 2018/0369021 A1    Dec. 27, 2018

(51) Int. Cl.
*G02C 5/00* (2006.01)
*A61F 9/02* (2006.01)

(52) U.S. Cl.
CPC .............. *G02C 5/008* (2013.01); *A61F 9/025* (2013.01); *A61F 9/026* (2013.01)

(58) Field of Classification Search
CPC ........ G02C 5/001; G02C 5/005; G02C 11/00; G02C 2200/16; A61F 9/026
USPC ........................................ 351/139, 154, 158
See application file for complete search history.

(56) References Cited

U.S. PATENT DOCUMENTS

| | | | |
|---|---|---|---|
| 4,222,640 A * | 9/1980 | Bononi | G02C 3/00 2/442 |
| 4,280,758 A | 7/1981 | Flader et al. | |
| 6,098,206 A | 8/2000 | Chou | |
| 6,139,144 A * | 10/2000 | Hynansky | A61F 9/026 351/158 |
| 7,431,452 B2 | 10/2008 | Sheldon | |
| 7,591,555 B1 | 9/2009 | Chen | |
| 8,087,776 B2 | 1/2012 | Pulito | |
| 8,142,014 B2 | 3/2012 | Hones | |
| 8,931,894 B1 | 1/2015 | Chen | |
| 2002/0029408 A1 | 3/2002 | Lindahl | |
| 2006/0098159 A1 | 5/2006 | Canavan et al. | |
| 2016/0193070 A1 | 7/2016 | Castillo | |

FOREIGN PATENT DOCUMENTS

| | | |
|---|---|---|
| CA | 2831450 A1 | 4/2014 |
| TW | M438639 | 10/2012 |

OTHER PUBLICATIONS

Vanos, R.; International Search Report from corresponding PCT Application No. PCT/CA2018/050774; search completed Aug. 2, 2018; dated Oct. 16, 2018, received by applicant Oct. 25, 2018.

* cited by examiner

*Primary Examiner* — Darryl J Collins

(57) ABSTRACT

There is provided an impact absorbing element for eyewear, comprising a compressible and deformable impact absorbing material sized to fit over at least a portion of a lower edge of a lens of the eyewear, the impact absorbing material comprising an outer portion and an inner portion, at least one of which is capable of deforming against a wearer of the eyewear when the eyewear experiences an impact. There is also provided eyewear comprising at least one lens; a frame supporting the at least one lens; and the impact absorbing element.

19 Claims, 10 Drawing Sheets

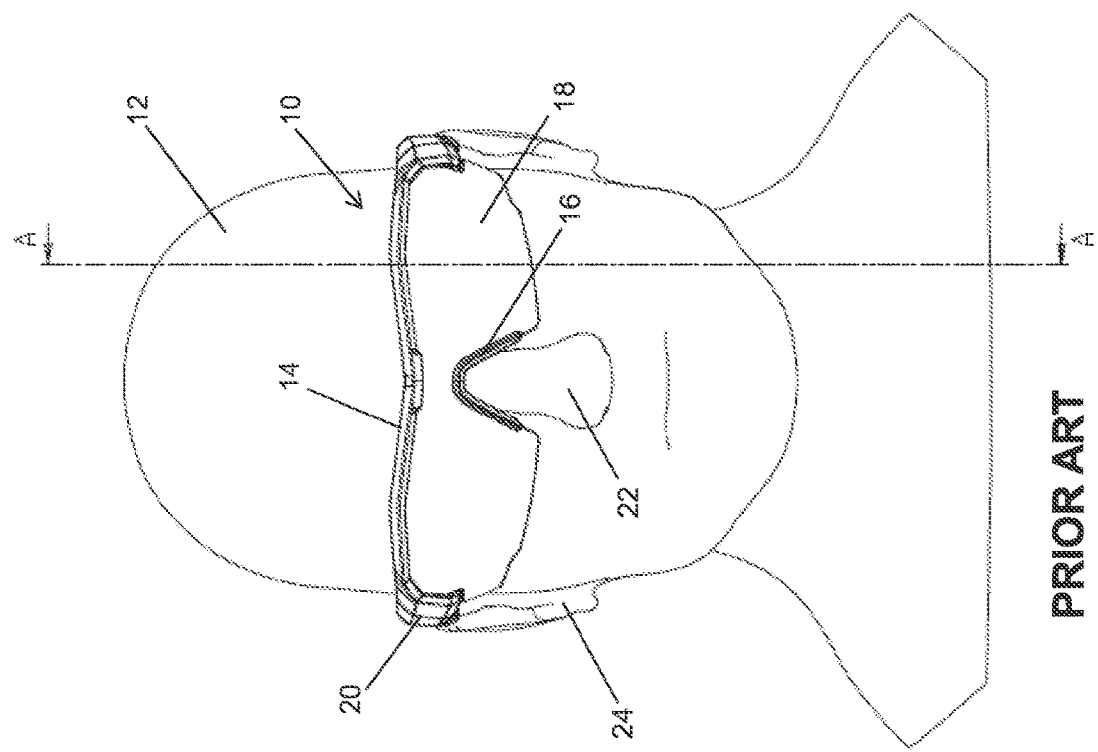
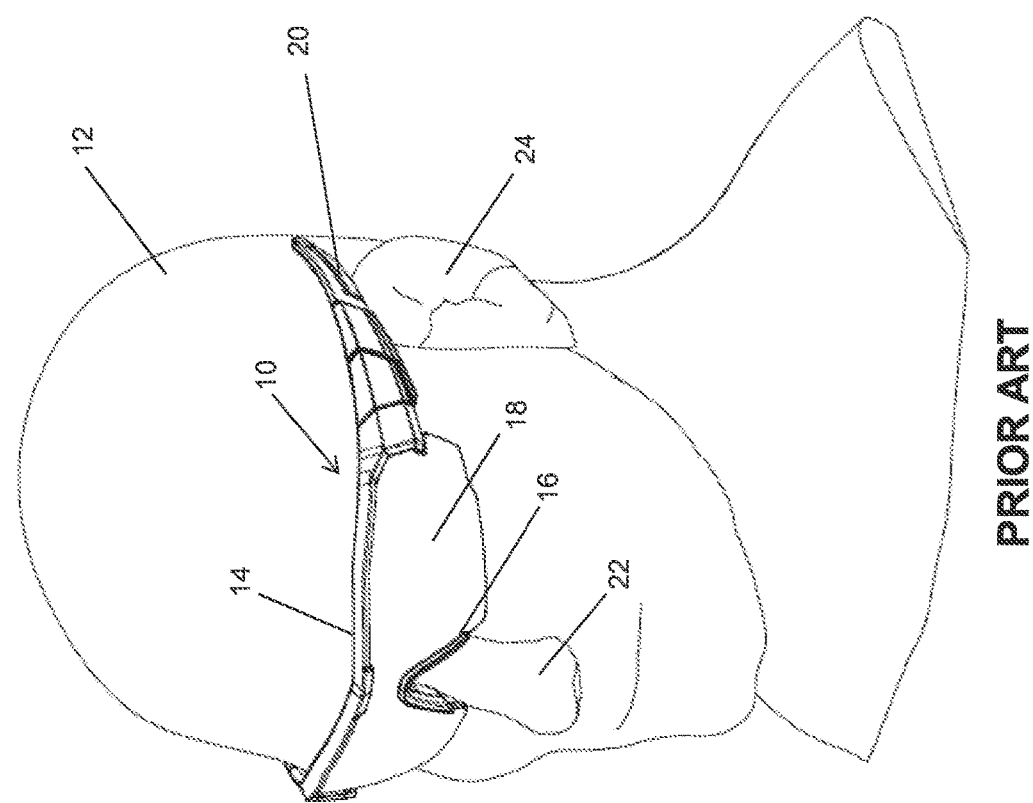

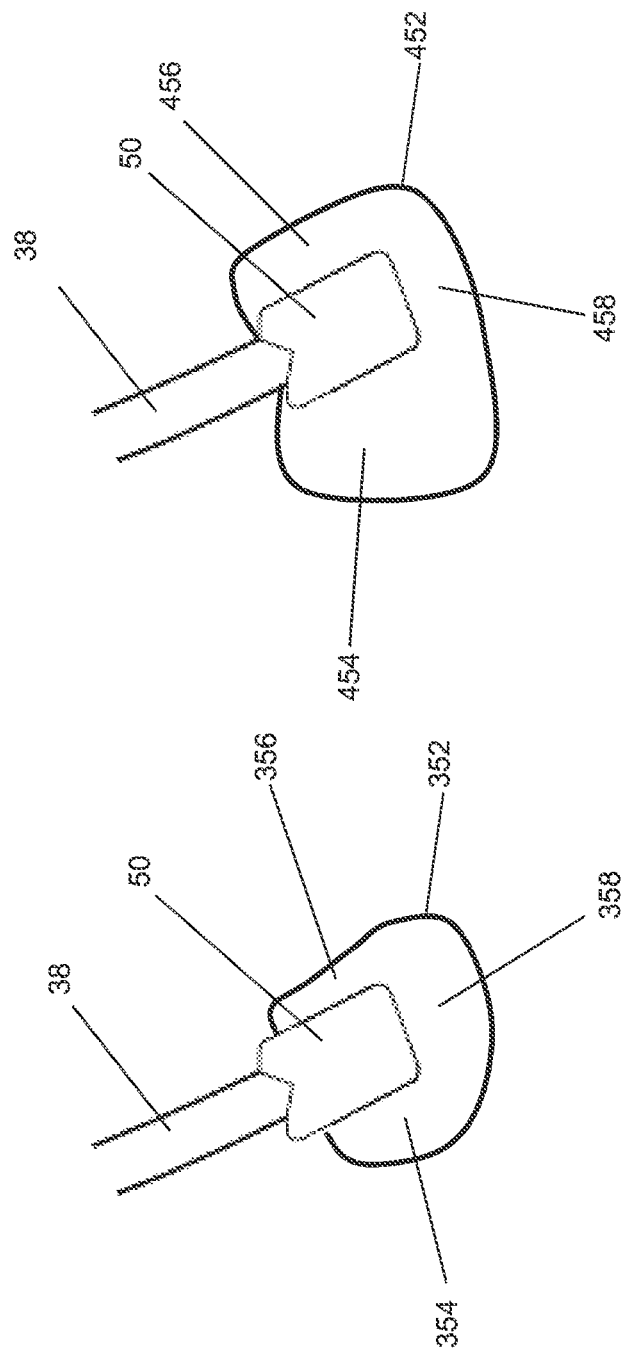

IMPACT ABSORBING ELEMENTS FOR EYEWEAR, INCLUDING OVERMOLDED EYEWEAR

TECHNICAL FIELD

The following relates to impact absorbing elements for eyewear, for example by overmolding eyewear with an impact absorbing material.

DESCRIPTION OF THE RELATED ART

Safety eyewear is required in various scenarios, such as on a job or construction site, shop or factory floor, etc. The purpose of safety eyewear is to protect the user from projectile objects, airborne debris, splashing fluid, etc.; that could come into contact with the user's eyes or areas of their face during use. Safety lenses can also be incorporated into other types of eyewear such as sports eyewear and the like.

FIGS. 1 and 2 illustrate an example of conventional safety eyewear 10 being worn by a user 12. The eyewear 10 is supported on the user 12 at least in part by resting the eyewear 10 on the user's nose 22. The safety eyewear 10 includes a frame 14 and a nose piece 16 that, in this example, secure and support a pair of lenses 18. The safety eyewear 10 also includes a pair of arms 20 that are either pivotally attached to, or integral with, the frame 14. The safety eyewear 10 can also be further supported on the user 12 by resting the arms 20 on the user's ears 24 and/or by engaging temple portions of the user's head 12 as is known in the art. The safety lenses 18 can be made from any suitable material providing impact and shatter resistance and, as illustrated in FIG. 1, these lenses 18 can partially wrap around the user's head 12 to provide side impact protection. The safety eyewear 10 shown in FIG. 1 includes a partial frame 14 that supports a plano-type lens 18.

The plano-type lens 18 includes an exposed or "bare" lower edge that can enter into contact with a user's facial area 28 as shown in the inset view in FIG. 3. Such contact can occur in various scenarios, for example as a result of an impact 26 on the eyewear 10. This scenario is not uncommon with safety eyewear 10, which is used, and is often required to be worn, for that very reason. Contact between the edge of a plano-type lens 18 and the user's face as illustrated in FIG. 3 is also known to cause potential injuries, or at least discomfort, to the user.

It is an object of the following to address at least one of the above-noted disadvantages.

SUMMARY

In one aspect, there is provided an impact absorbing element for eyewear, comprising a compressible and deformable impact absorbing material sized to fit over at least a portion of a lower edge of a lens of the eyewear, the impact absorbing material comprising an outer portion and an inner portion, at least one of which is capable of deforming against a wearer of the eyewear when the eyewear experiences an impact.

In another aspect, there is provided eyewear comprising: at least one lens; a frame supporting the at least one lens; and an impact absorbing element comprising a compressible and deformable impact absorbing material sized to fit over at least a portion of a lower edge of the lens, the impact absorbing material comprising an outer portion and an inner portion, at least one of which is capable of deforming against a wearer of the eyewear when the eyewear experiences an impact.

BRIEF DESCRIPTION OF THE DRAWINGS

Embodiments will now be described by way of example only with reference to the appended drawings wherein:

FIG. 1 is a perspective view of conventional safety eyewear worn by a user;

FIG. 2 is a front view of the safety eyewear of FIG. 1;

FIGS. 10($a$) and 10($b$) illustrate alternative configurations for impact absorbing portions of overmolded safety eyewear, alternatively provided as absorbing elements to be applied to safety eyewear;

DETAILED DESCRIPTION

Figure 3:
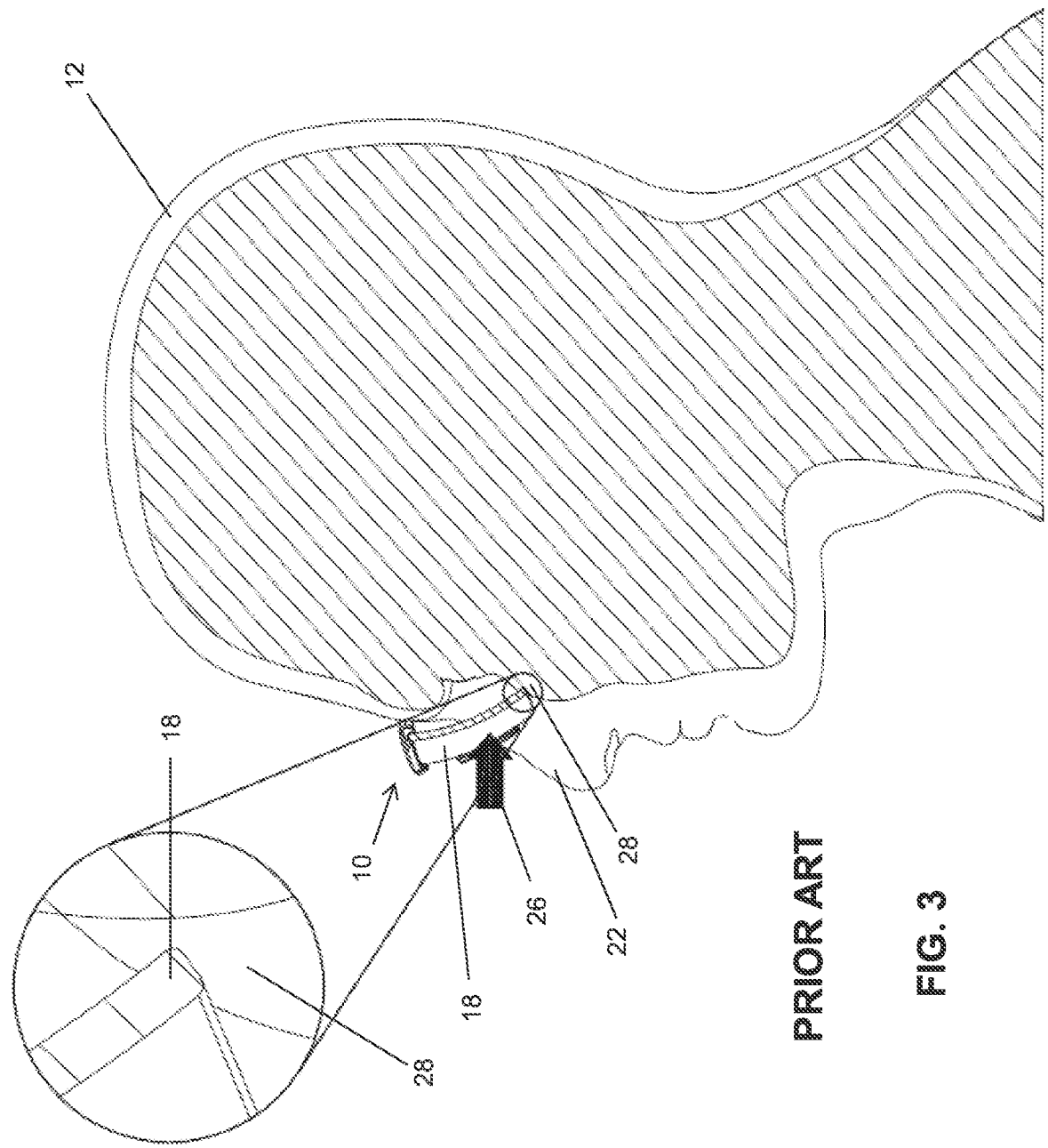
FIG. 3 is a cross-sectional side view of the conventional safety eyewear shown in FIGS. 1 and 2 illustrating an impact with the user in the inset view.
Figure 4:
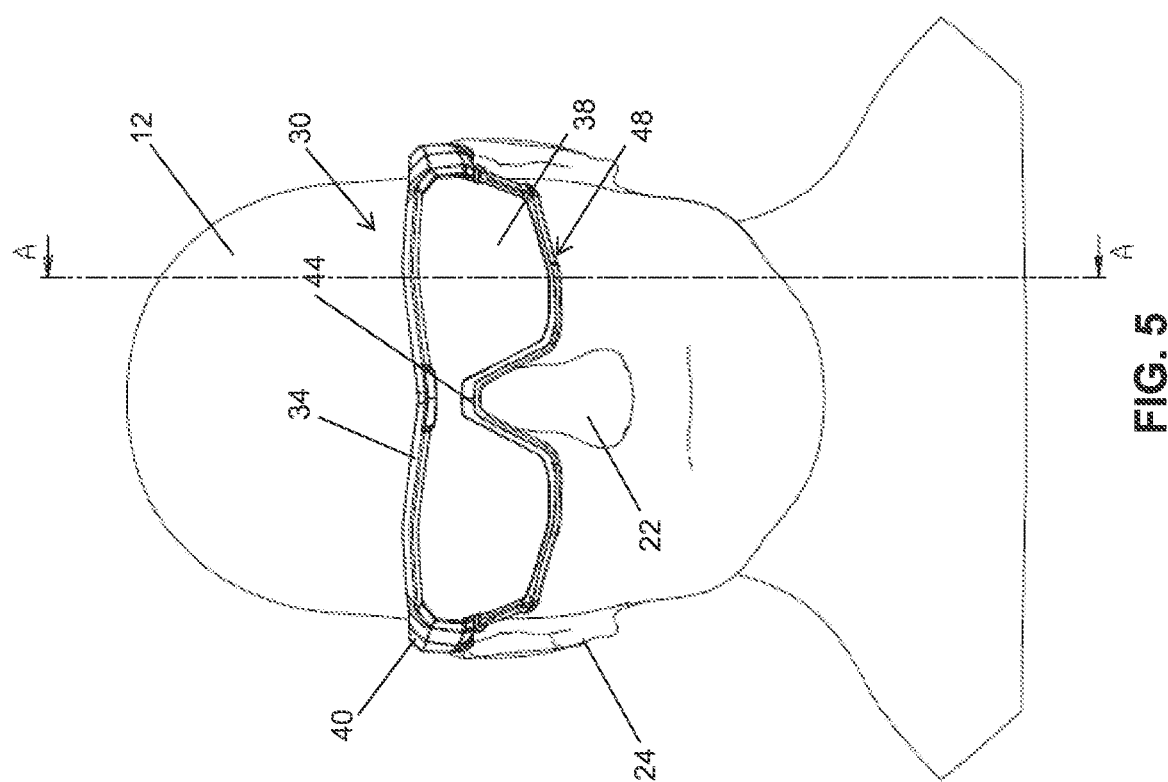
FIG. 4 is a perspective view of overmolded safety eyewear.
Figure 5:
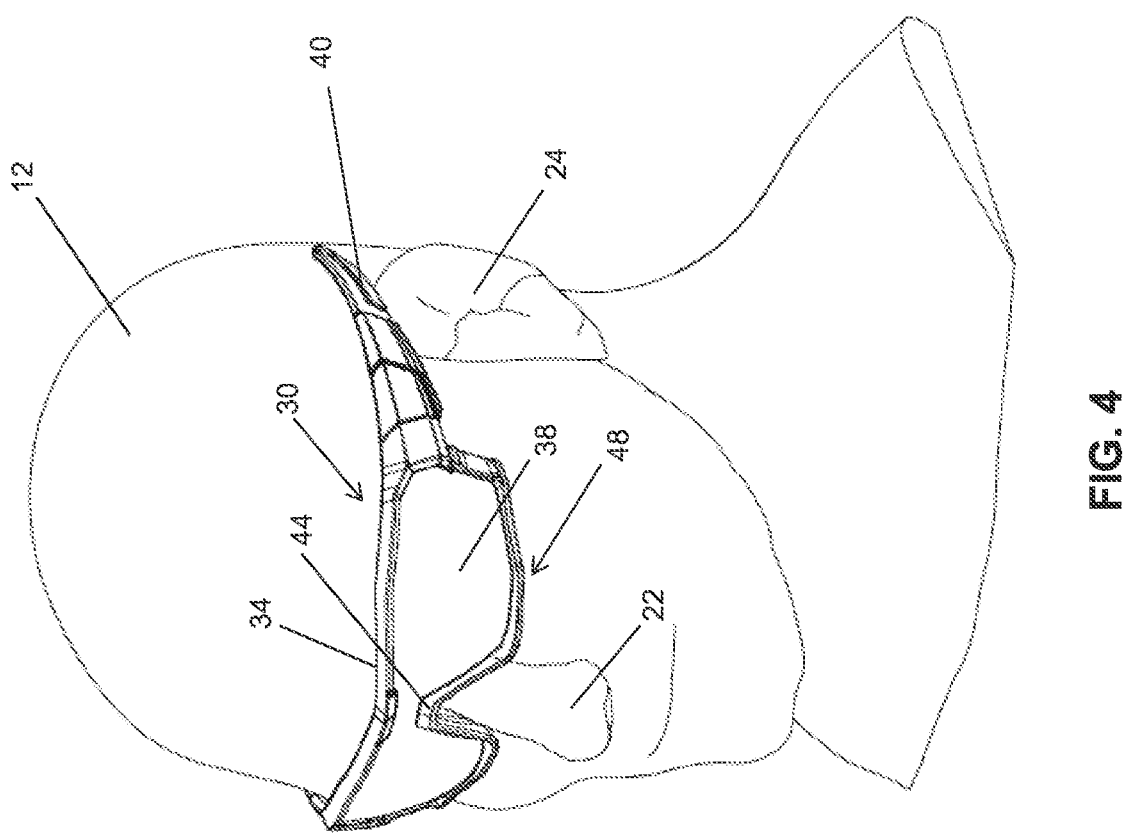
FIG. 5 is a front view of the overmolded safety eyewear of FIG. 4.
Figure 6:
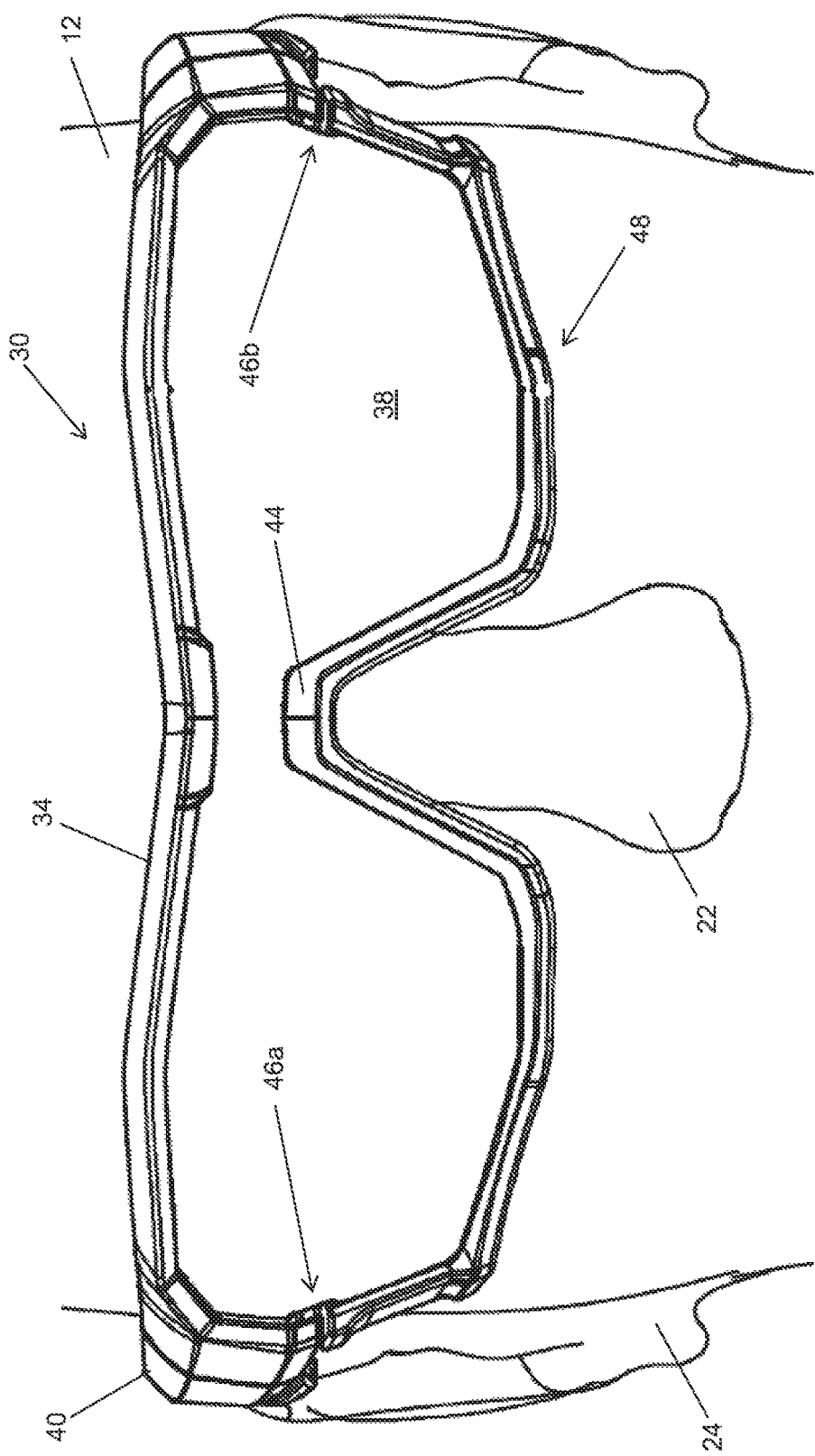
FIG. 6 is an enlarged front view of an overmolded safety eyewear frame.

To address the aforementioned problems that can arise with the exposed lower edges of plano-type lenses 18, at least a portion of that lower edge can be overmolded, or an impact absorbing element attached thereto. Turning now to FIGS. 4 to 6, overmolded safety eyewear 30 is shown being worn by a user 12. The eyewear 30 is supported on the user 12 at least in part by resting the eyewear 30 on the user's nose 22. The overmolded safety eyewear 30 includes a frame 34 and a pair of arms 40. The arms 40 are either pivotally attached to, or integral with, the frame 34. The safety eyewear 30 can at least in part be supported on the user 12 by resting the arms 40 on the user's ears 24 and/or by engaging temple portions of the user's head 12. The frame 34 supports or contains safety lenses 38, which can be made from any suitable material providing impact and shatter resistance. As illustrated in FIG. 4, these lenses 38 can partially wrap around the user's head 12 to provide side impact protection.

The safety eyewear 30 shown in FIGS. 4 to 6 includes a partial frame 34 that supports a plano-type lens 38. However, in contrast to the eyewear 10 shown in FIG. 1, the eyewear 30 includes at least one impact absorbing element 48. In this example, a single continuous impact absorbing element 48 is overmolded on the eyewear 30, and follows the contours of the lower edge of the plano-type lens 38. The element 48 is also shaped to provide a nose piece 44 for supporting the eyewear 30 on the user's nose 22 without directly contacting the lens 38.

Figure 7:
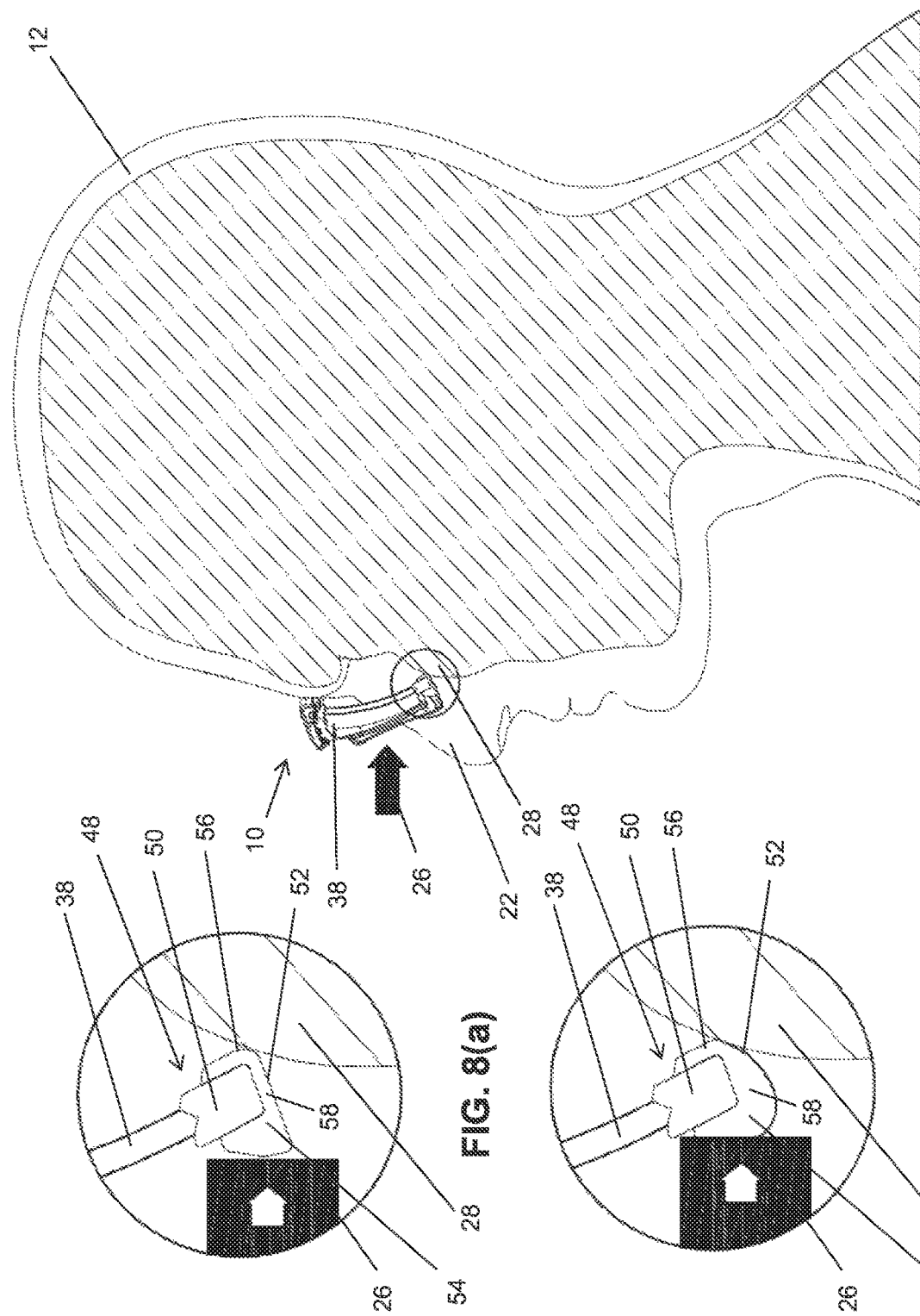
FIG. 7 is a cross-sectional side view of the overmolded safety eyewear shown in FIGS. 4, 5 and 6, illustrating absorption of an impact by an overmolded portion in the inset view.

As seen in FIG. 6, the impact absorbing element 48 in this example has a pair of termination points 46*a*, 46*b* on opposite sides of the frame 34. The termination points 46*a*, 46*b* are adjacent the frame 34 to appear as a substantially continuous frame about the lens 38. In this way, a substantially uniform look for the frame 34 can be provided while using two different materials, one for supporting/containing the lens 38 (i.e. the frame 34), and the other for providing the impact absorption capabilities discussed herein (i.e. the element 48). As will be discussed below, the substantially continuous look is only one example, and the element 48 can instead cover any portion of the lower edge of the lens 38 such that it is or becomes interposed between the lens 38 and the facial area 28 upon the eyewear 30 experiencing an impact 26 as illustrated in FIG. 7. While the examples described herein are made in the context of safety eyewear 30, it can be appreciated that any type of eyewear can benefit from having the impact absorbing element 48 applied thereto (or incorporated therewith), for example, prescription glasses having a complete rim, sports eyewear, etc.

Figure 8:
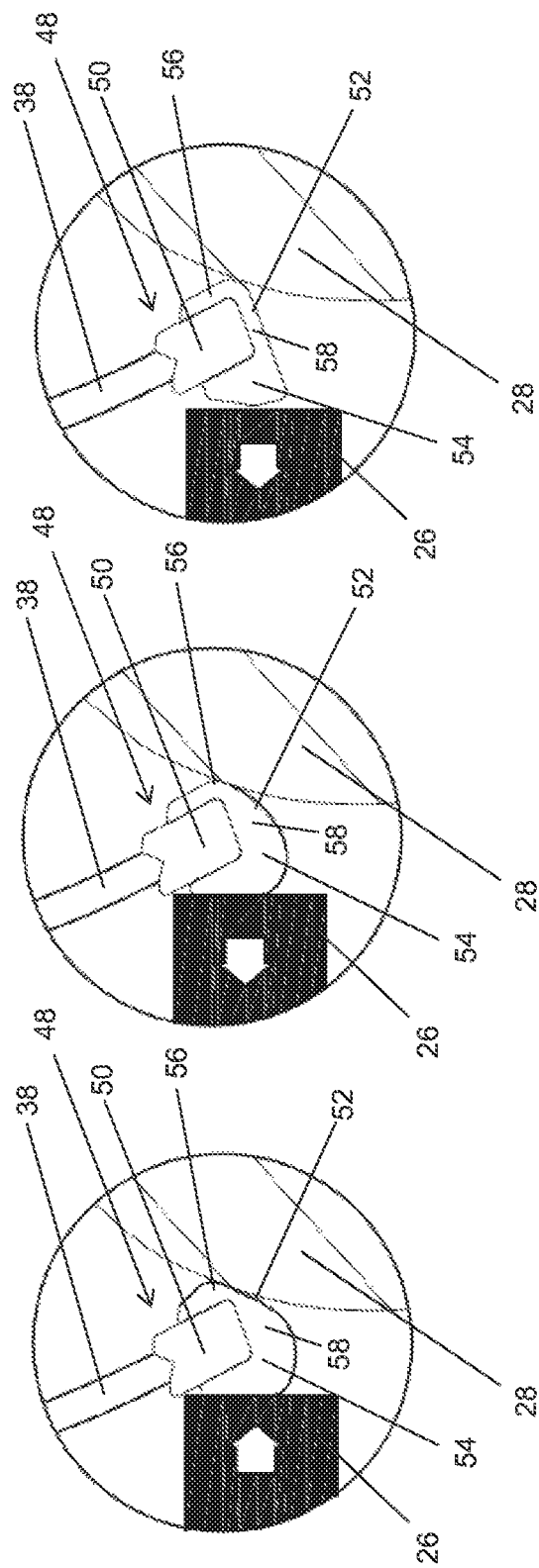
FIGS. 8($a$) through 8($e$) provide a series of enlarged side views illustrating absorption of an impact by the overmolded portion shown in FIG. 6.

Turning now to FIG. 8(*a*), an enlarged view of the impact absorbing element 48 is shown. In this example, the impact absorbing element 48 includes a relatively rigid rim 50 that is attached along the lower edge of the lens 38. It can be appreciated that the rim 50 can be separate from, or integral with, the frame 34. The rim 50 provides an interface between the lens 38 and the element 48, and can be overmolded with an impact absorbing material 52. Overmolding, sometimes referred to as two times injection molding, is a process where a single part is created using two or more different materials in combination. Typically, the first material (or substrate) is partially or fully covered by overmolded material during the manufacturing process. In this case, the rim 50 acts as the substrate that is overmolded with the impact absorbing material 52, which is generally a softer plastic, rubber, or elastomer (e.g., TPE), or other suitable material. It can be appreciated that the rim 50 can be overmolded prior to or after being affixed to the lens 38. In the cross-sectional view shown in FIG. 8(*a*), it can be seen that the impact absorbing material 52 includes an outer portion 54, an inner portion 56, and a lower portion 58. The material 52 is therefore advantageously applied to the bottom edge of the lens(es) 38 such that a portion is aligned or positioned to engage the facial area 28 of the user on impact, with another portion aligned or positioned opposite that portion to absorb the impact, with the portions deforming during impact to disperse the forces along the length of the material 52.

In FIG. 8(*a*), an impact 26 is shown at or near the bottom portion of the plano-type lens 38, e.g., near or on the outer portion 54 of the impact absorbing material 52. Due to the compressibility of the material 52, the outer portion 54 begins to deform as shown in FIG. 8(*b*) while absorbing the impact 26. Since the material 52 is bonded to the rim 50, as the outer portion 54 deforms, the inner and lower portions 56, 58 also begin to deform during the impact, as shown in FIGS. 8(*b*) and 8(*c*). As such, not only does the compressibility of the material 52 absorb the forces of the impact 26 along the rim 50, the deformability of the material 52 causes additional material 52 to move towards and possibly press against the facial area 28, rather than the rim 50 or lens 38. As illustrated in FIGS. 8(*d*) and 8(*e*), as the impact 26 retreats or otherwise ceases to occur, the material 52 can reform as is appeared prior to the impact.

Figure 9:
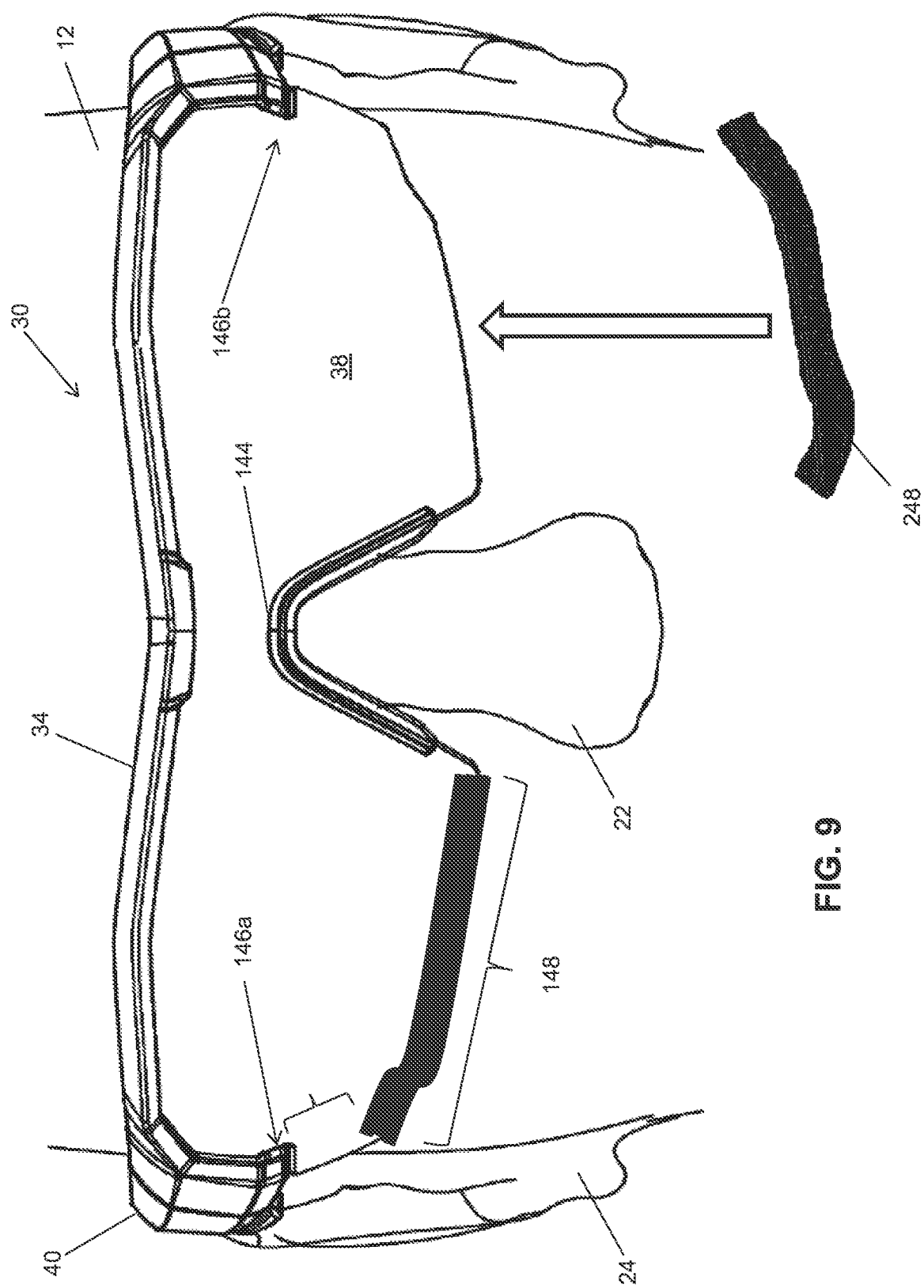
FIG. 9 is an enlarged front view illustrating alternative impact absorbing elements for safety eyewear.

While the impact absorbing element 48 can be provided along any portion of the lens 38, it can be appreciated that by having the element 48 extend along substantially the entire bottom edge of the lens 38 as shown in FIG. 6, a greater amount of energy from the impact 26 can be absorbed, the impact can be dispersed along a wider area, and a greater amount of material 52 is available to cushion the impact against the facial area(s) 28. For example, the element 148 shown in the left area of FIG. 9 is not continuous along the entire bottom edge of the lens 38, but extends along a broad enough area to provide sufficient cushioning against an impact, particularly near the user's cheekbones.

It can be appreciated that the impact absorbing element 48 can also be added to existing stock of safety eyewear 10 with plano-type lenses 18 to create or retrofit existing eyewear to provide the overmolded safety eyewear 30 shown in FIG. 4. This can be done by overmolding the impact absorbing material 52 onto the rim 50 to create an attachable element 248 that is affixed to the lower edge of the lens 38 as shown in the right area of FIG. 9. The element 248 shown in FIG. 9 is only one implementation. For example, a complete continuous piece much like what is shown in FIG. 6 can also be added to eyewear 30 that does not yet include a nose piece 144, or by removing such a nosepiece 144 or integrating the nosepiece 144 into the attachable element 248. As such, the impact absorbing element 48 can be created and incorporated into eyewear 30 in numerous ways.

The shape taken by the impact absorbing material 52 can also vary and what is shown in FIG. 8 is only illustrative. For example, material 352 shown in FIG. 10(*a*) can be made to be bulkier around the rim 50 to provide additional cushioning against impacts 26. FIG. 10(*b*) shows an example wherein a bulkier outer portion 454 is used and the material 452 completely covers the rim 50 such that is in not visible to the user. As such, it can be appreciated that the shape of the material 52 and amounts dedicated to the different portions 54, 56, 58 can vary, depending on the look and feel desired, and the amount of cushioning desired (e.g., heavier duty versus lighter duty options), etc.

It can also be appreciate that for eyewear 30 that already includes a rim 50 along the bottom edge of the lens 38, one can overmold the existing rim 50 or add or affix an impact absorbing element 48 without using an overmolding process. That is, while examples herein discuss applying the material 52 by overmolding, the material 52 can instead be formed and mechanically applied separately using an adhesive or other affixing means.

Figure 11:
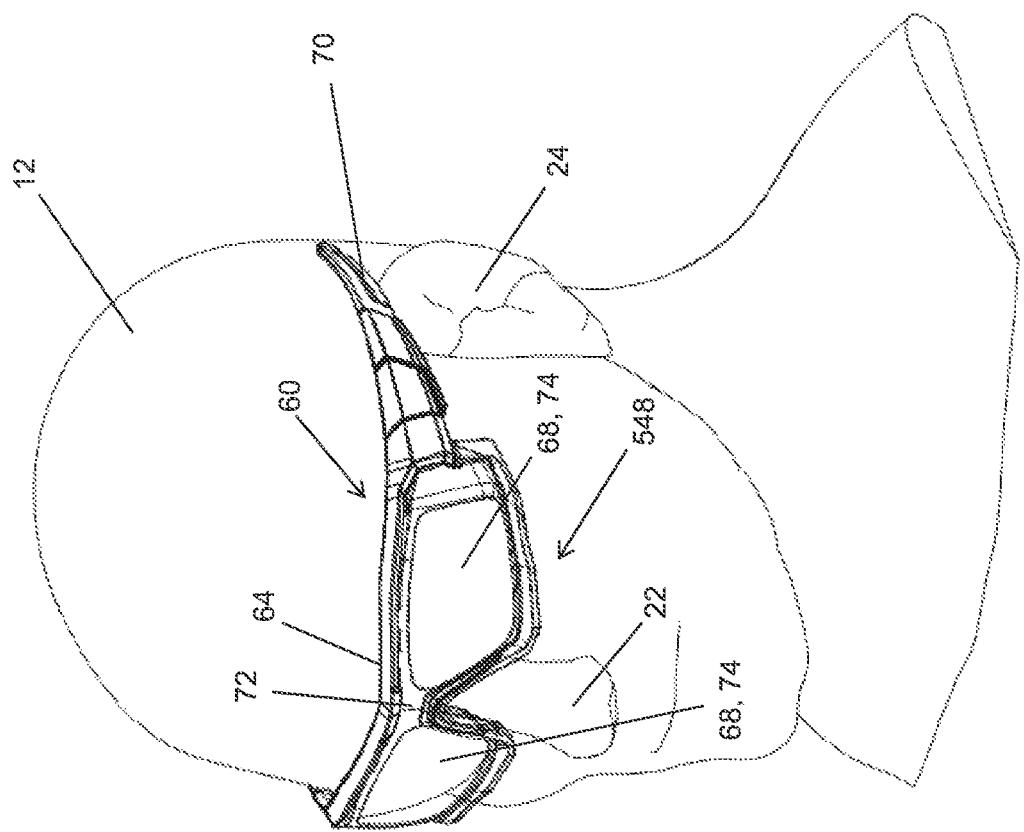
FIG. 11 is a perspective view of overmolded prescription carrying safety eyewear.

Other types of safety eyewear can benefit from incorporating an impact absorbing element. For example, in FIGS. 11 to 13 overmolded prescription carrier safety eyewear 60 is shown, being worn by a user 12. The eyewear 60 is supported on the user 12 at least in part by resting the eyewear 60 on the user's nose 22. The eyewear 60 includes a frame 64 and a pair of arms 70. The arms 70 are either pivotally attached to, or integral with, the frame 64. The safety eyewear 60 can at least in part be supported on the user 12 by resting the arms 70 on the user's ears 24 and/or by engaging temple portions of the user's head 12. The frame 64 supports or contains safety lenses 64, which can be made from any suitable material providing impact and shatter resistance. As illustrated in FIG. 11, these lenses 68 can partially wrap around the user's head 12 to provide side impact protection. The frame 64 can also support one or more prescription lenses 74 behind the safety lenses 38.

Figure 12:
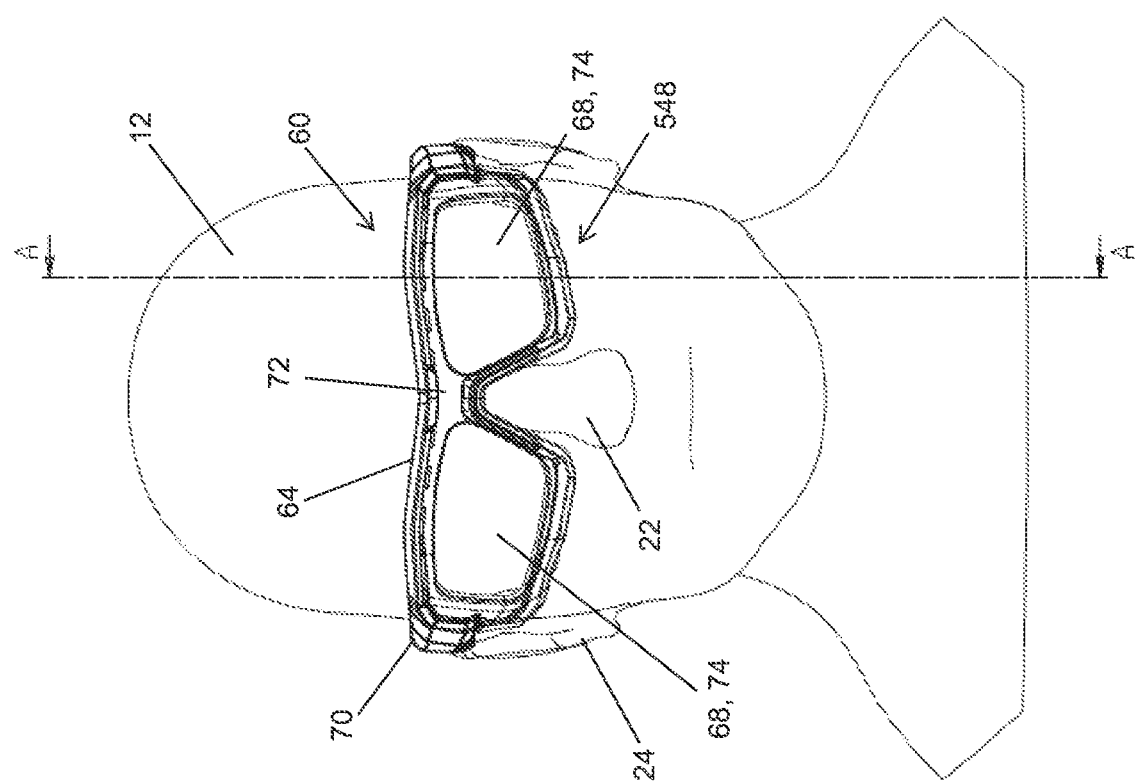
FIG. 12 is a front view of the overmolded prescription carrying safety eyewear of FIG. 11.
Figure 13:
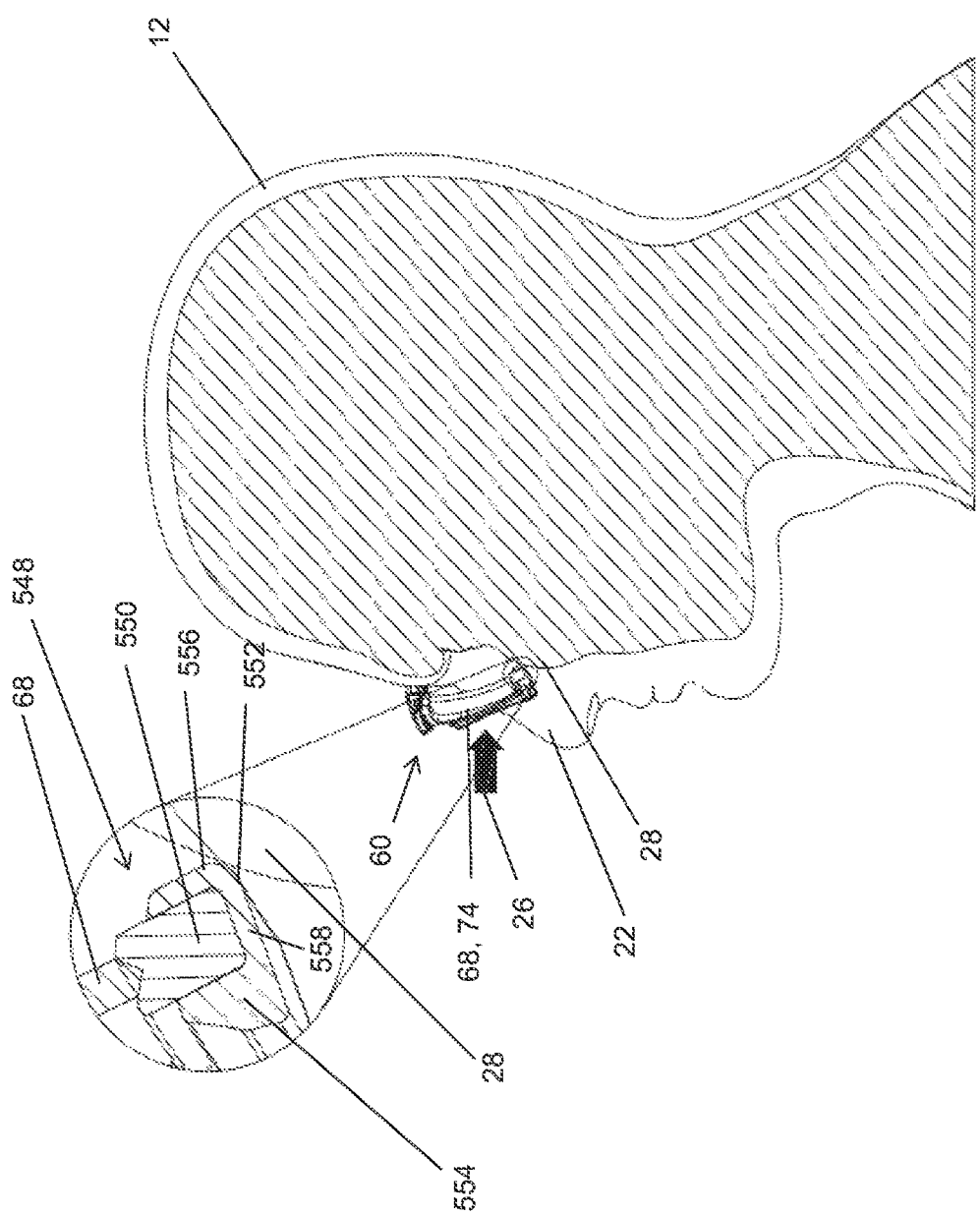
FIG. 13 is a cross-sectional side view of the overmolded prescription carrying safety eyewear shown in FIGS. 11 and 12 illustrating absorption of an impact by an overmolded portion in the inset view.

The safety eyewear 60 shown in FIGS. 11 to 13 includes a partial frame 64 that supports a plano-type lens 68. However, similar to what is shown in FIG. 4 and in contrast to the eyewear 10 shown in FIG. 1, the eyewear 60 includes at least one impact absorbing element 548. In this example, a single continuous impact absorbing element 548 follows the contours of the lower edge of the plano-type lens 68. The element 548 thus also provides a nose piece 64 for supporting the eyewear 60 on the user's nose 22 without directly contacting the lens 68. As shown in FIG. 13, the impact absorbing element 548 can include an impact absorbing material 552 over a rim 550, the material 552 including an outer portion 554, inner portion 556, and a lower portion 558, similar to the implementation shown in FIG. 4.

For simplicity and clarity of illustration, where considered appropriate, reference numerals may be repeated among the figures to indicate corresponding or analogous elements. In addition, numerous specific details are set forth in order to provide a thorough understanding of the examples described herein. However, it will be understood by those of ordinary skill in the art that the examples described herein may be practiced without these specific details. In other instances, well-known methods, procedures and components have not been described in detail so as not to obscure the examples described herein. Also, the description is not to be considered as limiting the scope of the examples described herein.

It will be appreciated that the examples and corresponding diagrams used herein are for illustrative purposes only. Different configurations and terminology can be used without departing from the principles expressed herein. For instance, components and modules can be added, deleted, modified, or arranged with differing connections without departing from these principles.

Although the above principles have been described with reference to certain specific examples, various modifications thereof will be apparent to those skilled in the art as outlined in the appended claims.

The invention claimed is:

1. An impact absorbing element for eyewear comprising a compressible and deformable impact absorbing material bonded to and sized to fit over at least a portion of a lower edge of a lens or frame of the eyewear to cover both a front portion of the lens or frame and a rear portion of the lens or frame, the impact absorbing material comprising an outer portion over the front portion of the lens or frame and an inner portion over the rear portion of the lens or frame;
wherein the outer portion is relatively larger than the inner portion at least prior to an impact;
wherein the outer portion deforms in response to the impact while the inner portion deforms during the impact thereby causing a portion of the relatively larger outer portion of the impact absorbing material to move towards a wearer;
and wherein the impact absorbing material at least partially reforms subsequent to the impact.

2. The element of claim 1, wherein the impact absorbing material further comprises a lower portion extending between the inner and outer portions, wherein as the outer portion deforms under impact, at least one of the lower portion and the inner portion deforms against the wearer to absorb forces imparted by the impact.

3. The element of claim 1, wherein the impact absorbing material extends laterally along substantially the entire length of the bottom edge of the lens.

4. The element of claim 1, wherein the impact absorbing material is overmolded onto the eyewear.

5. The element of claim 4, wherein the impact absorbing material is overmolded onto a rim extending along the at least a portion of the lower edge of the lens.

6. The element of claim 1, wherein the impact absorbing material is mechanically affixed to the lens.

7. The element of claim 6, wherein the impact absorbing material is mechanically affixed to a rim, the rim extending along the at least a portion of the lens.

8. Eyewear comprising:
at least one lens;
a frame supporting the at least one lens; and
an impact absorbing element comprising a compressible and deformable impact absorbing material bonded to and sized to fit over at least a portion of a lower edge of the lens or frame to cover both a front portion of the lens or frame and a rear portion of the lens or frame, the impact absorbing material comprising an outer portion over the front portion of the lens or frame and an inner portion over the rear portion of the lens or frame,
wherein the outer portion is relatively larger than the inner portion at least prior to an impact;
wherein the outer portion deforms in response to the impact while the inner portion deforms during the impact thereby causing a portion of the relatively larger outer portion of the impact absorbing material to move towards a wearer;
and wherein the impact absorbing material at least partially reforms subsequent to the impact.

9. The eyewear of claim 8, wherein the impact absorbing element provides a nose bridge for supporting the frame on a user.

10. The eyewear of claim 8, further comprising a pair of arms coupled to the frame.

11. The eyewear of claim 8, wherein the eyewear is safety eyewear.

12. The eyewear of claim 11, configured to carry a prescription lens behind the lens.

13. The eyewear of claim 8, wherein the impact absorbing material further comprises a lower portion extending between the inner and outer portions, wherein as the outer portion deforms under impact, at least one of the lower portion and the inner portion deforms against the wearer to absorb forces imparted by the impact.

14. The eyewear of claim 8, wherein the impact absorbing material extends laterally along substantially the entire length of the bottom edge of the lens.

15. The eyewear of claim 8, wherein the impact absorbing material is overmolded onto the eyewear.

16. The eyewear of claim 15, wherein the impact absorbing material is overmolded onto a rim extending along the at least a portion of the lower edge of the lens.

17. The eyewear of claim 8, wherein the impact absorbing material is mechanically affixed to the lens.

18. The eyewear of claim 17, wherein the impact absorbing material is mechanically affixed to a rim, the rim extending along the at least a portion of the lens.

19. The eyewear of claim 8, wherein the at least one lens is/are a plano-type lens.

* * * * *